United States Patent
Chewter et al.

(10) Patent No.: US 8,598,398 B2
(45) Date of Patent: Dec. 3, 2013

(54) PROCESS FOR THE PREPARATION OF AN OLEFIN

(75) Inventors: Leslie Andrew Chewter, Amsterdam (NL); Michiel Johannes Franciscus Maria Verhaak, Amsterdam (NL); Jeroen Van Westrenen, Amsterdam (NL)

(73) Assignee: Shell Oil Company, Houston, TX (US)

( * ) Notice: Subject to any disclaimer, the term of this patent is extended or adjusted under 35 U.S.C. 154(b) by 854 days.

(21) Appl. No.: 12/301,143

(22) PCT Filed: May 16, 2007

(86) PCT No.: PCT/EP2007/054741
§ 371 (c)(1),
(2), (4) Date: Nov. 17, 2008

(87) PCT Pub. No.: WO2007/135045
PCT Pub. Date: Nov. 29, 2007

(65) Prior Publication Data
US 2009/0187059 A1    Jul. 23, 2009

(30) Foreign Application Priority Data
May 19, 2006   (EP) .................................... 06114283

(51) Int. Cl.
*C07C 1/20*   (2006.01)
(52) U.S. Cl.
USPC .............................. 585/640; 585/638; 585/639
(58) Field of Classification Search
USPC ................................... 585/638, 639, 640, 809
See application file for complete search history.

(56) References Cited

U.S. PATENT DOCUMENTS

| | | | |
|---|---|---|---|
| 679,851 A | 8/1901 | Leckband | |
| 4,025,576 A * | 5/1977 | Chang et al. | 585/322 |
| 4,076,842 A | 2/1978 | Plank et al. | 423/328 |
| 4,197,185 A | 4/1980 | Le Page et al. | 208/71 |
| 4,397,827 A | 8/1983 | Chu | 423/326 |
| 4,542,252 A * | 9/1985 | Graziani et al. | 585/640 |
| 4,544,792 A | 10/1985 | Smith et al. | 545/533 |
| 4,556,477 A | 12/1985 | Dwyer | 208/111 |
| 4,590,320 A * | 5/1986 | Sapre | 585/324 |
| 4,626,415 A | 12/1986 | Tabak | 422/190 |
| 4,684,757 A | 8/1987 | Avidan et al. | 585/331 |

(Continued)

FOREIGN PATENT DOCUMENTS

| | | | | |
|---|---|---|---|---|
| DE | 10043644 | 3/2002 | | C07C 29/128 |
| EP | 109059 | 5/1984 | | C07C 11/06 |

(Continued)

OTHER PUBLICATIONS

Obenaus, et al., "Butenes" in Ullmann's Encyclopedia of Industrial Chemistry, 2002, Wiley-VCH, available on-line Jun. 15, 2000.*
Meier, et al: "Atlas of Zeolite Structure Types Passage", Atlas of Zeolite Framework Types, 2001, pp. 9-20.

*Primary Examiner* — In Suk Bullock
*Assistant Examiner* — Bradley Etherton

(57) ABSTRACT

Process for the preparation of ethylene and/or propylene comprising reacting an oxygenate feed and an olefinic co-feed in a reactor in the presence of a zeolite catalyst to prepare an olefinic reaction mixture; wherein the olefinic co-feed is partially obtained from an olefinic refinery stream and partially obtained from a olefinic recycle stream.

10 Claims, 1 Drawing Sheet

(56) References Cited

U.S. PATENT DOCUMENTS

| | | | |
|---|---|---|---|
| 5,210,364 A * | 5/1993 | Barri et al. | 585/640 |
| 6,307,117 B1 | 10/2001 | Tsunoda et al. | 585/651 |
| 6,339,181 B1 | 1/2002 | Chen et al. | 585/653 |
| 6,372,949 B1 * | 4/2002 | Brown et al. | 585/639 |
| 6,517,807 B2 | 2/2003 | Verduijn et al. | 423/709 |
| 6,656,345 B1 | 12/2003 | Chen et al. | 208/120.01 |
| 6,858,129 B2 | 2/2005 | Mohr et al. | 208/120.01 |
| 6,888,038 B2 * | 5/2005 | Powers et al. | 585/648 |
| 7,112,307 B2 | 9/2006 | Abrevaya et al. | 422/142 |
| 7,314,964 B2 | 1/2008 | Abrevaya et al. | 585/651 |
| 2002/0063082 A1 | 5/2002 | Touvelle et al. | 208/134 |
| 2002/0115898 A1 * | 8/2002 | Searle | 585/639 |
| 2003/0078463 A1 | 4/2003 | Martens et al. | 585/638 |
| 2003/0125598 A1 | 7/2003 | Chisholm et al. | 585/640 |
| 2003/0181777 A1 | 9/2003 | Powers et al. | 585/648 |
| 2004/0015028 A1 | 1/2004 | Brown et al. | 585/520 |
| 2005/0070422 A1 | 3/2005 | Chen et al. | 502/64 |
| 2005/0130832 A1 | 6/2005 | Abrevaya et al. | 502/4 |

FOREIGN PATENT DOCUMENTS

| | | | |
|---|---|---|---|
| EP | 485145 | 5/1992 | C07C 11/02 |
| EP | 788838 | 8/1997 | C10G 35/095 |
| EP | 921181 | 6/1999 | C10G 11/05 |
| GB | 663901 | 12/1951 | |
| WO | WO9957085 | 11/1999 | C07C 4/02 |
| WO | WO9957226 | 11/1999 | C10G 11/05 |
| WO | WO0026163 | 5/2000 | C07C 4/02 |
| WO | WO0129152 | 4/2001 | C10G 3/00 |
| WO | WO 2001023500 | 4/2001 | C10G 3/00 |
| WO | WO0134730 | 5/2001 | C10G 51/00 |
| WO | WO0181280 | 11/2001 | C07C 11/06 |
| WO | WO0190279 | 11/2001 | C10G 11/18 |
| WO | WO0210098 | 2/2002 | C07C 1/20 |
| WO | WO03020667 | 3/2003 | C07C 2/08 |
| WO | WO2004018392 | 3/2004 | C07C 11/02 |
| WO | WO2005016856 | 2/2005 | C07C 1/20 |
| WO | WO2005028594 | 3/2005 | C10G 11/16 |

* cited by examiner

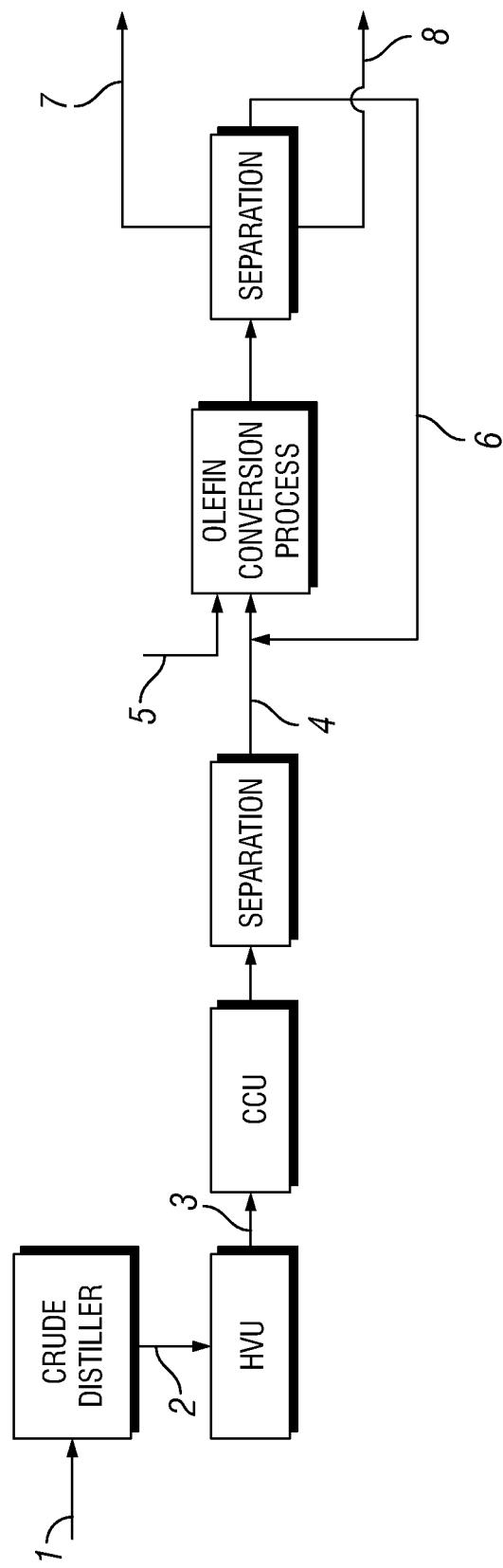

PROCESS FOR THE PREPARATION OF AN OLEFIN

The present application claims priority to European Patent Application 06114283.2 filed 19 May 2006.

FIELD OF THE INVENTION

This invention relates to a process for the preparation of an olefin, such as ethene and/or propene.

BACKGROUND OF THE INVENTION

Processes for the preparation of olefins are known in the art.

US2003/0181777 describes a process wherein a conventional stream cracker C4-Raffinate-2, containing isobutane, 1-butene, n-butane, trans-2-butene and cis-2-butene, is contacted with a MTT type zeolite in the presence of a co-feed of methanol.

The process of US2003/0181777 requires a continuous stream of olefins, as without olefins the therein described cracking process can not be carried out. That is, variations in the amount of olefins fed, will have a large influence on the process.

At many refinery sites small waste streams containing $C_4$ and $C_5$ olefins are generated. Presently such olefins are blended into product fractions, converted into fuel components or sometimes even hydrogenated and used as fuel.

It would be desirable to be able to convert such "waste" olefins into valuable ethylene and propylene. Unfortunately such waste streams may not always be present as a continuous stream. The amounts in which such waste streams can be provided may vary widely in time and location. Processes such as those described in US2003/0181777, however, require a continuous feed stream.

It would therefore be desirable to have a process which allows one to process "waste" olefins, even if such "waste" olefins are provided as non-continuous stream.

SUMMARY OF THE INVENTION

A process enabling one convert low value "waste" olefins into high value ethylene and propylene at one's convenience has now been found.

Accordingly the present invention provides a process for the preparation of ethylene and/or propylene comprising reacting an oxygenate feed and an olefinic co-feed in a reactor in the presence of a zeolite catalyst to prepare an olefinic reaction mixture;
wherein the olefinic co-feed is partially obtained from an olefinic refinery stream and partially obtained from a olefinic recycle stream.

Such a process allows one to convert low value "waste" olefins into high value ethylene and propylene at any point in time and independent of the amount of "waste" olefin supplied.

A further advantage is that the process is more environmentally friendly. The production of olefin in catalytic crackers or stream crackers produces environmentally unfriendly carbondioxide via the burning of fuel. When "waste" olefins, often produced in a first thermal or catalytic cracker are converted to ethylene and propylene in a second thermal or catalytic cracker, more such carbon dioxide is produced. By converting the waste olefins into ethylene and/propylene with the process according to the invention the amount of carbon dioxide generated per ton of product can be greatly reduced.

DETAILED DESCRIPTION OF THE INVENTION

By an olefinic co-feed is understood a feed containing one or more olefins.

The olefinic co-feed can contain one olefin or a mixture of olefins. Preferably the olefinic co-feed contains a mixture of olefins. Apart from olefins, the olefinic co-feed may contain other hydrocarbon compounds, such as for example paraffinic, alkylaromatic, aromatic compounds or a mixture thereof. Preferably the olefinic co-feed comprises more than 50 wt %, more preferably more than 80 wt %, still more preferably more than 90 wt % and most preferably in the range from 95 to 100 wt % of olefin(s). An especially preferred olefinic co-feed consists essentially of olefin(s).

Any non-olefinic compounds in the olefinic co-feed are preferably paraffinic compounds. If the olefinic co-feed contains any non-olefinic hydrocarbon, these are preferably paraffinic compounds. Such paraffinic compounds are preferably present in an amount in the range from 0 to 10 wt %, more preferably in the range from 0 to 5 wt %, still more preferably in the range from 0 to 1 wt % and most preferably in an amount of less than 0.5 wt %.

By an olefin is understood an organic compound containing at least two carbon atoms connected by a double bond. A wide range of olefins can be used. The olefin can be a mono-olefin, having one double bond, or a poly-olefin, having two or more double bonds. Preferably olefins present in the olefinic co-feed are mono-olefins.

The olefin(s) can be a linear, branched or cyclic olefin. Preferably olefins present in the olefinic co-feed are linear or branched olefins.

Preferred olefins have in the range from 4 to 12, preferably in the range from 4 to 10, and more preferably in the range from 4 to 8 carbon atoms.

Examples of suitable olefins that may be contained in the olefinic co-feed include 1-butene, 2-butene, iso-butene (2-methyl-1-propene), 1-pentene, 2-pentene, 2-methyl-1-butene, 2-methyl-2-butene, 3-methyl-1-butene, 3-methyl-2-butene, 1-hexene, 2-hexene, 3-hexene, 2-methyl-1-pentene, 2-methyl-2-pentene, 3-methyl-1-pentene, 3-methyl-2-pentene, 4-methyl-1-pentene, 4-methyl-2-pentene, 2,3-dimethyl-1-butene, 2,3-dimethyl-2-butene, 3,3-dimethyl-1-butene, heptenes, octenes, nonenes and decenes. Of these, butenes and pentenes are preferred. Ethene and propene may be present in the olefinic co-feed. As the purpose of the process is to prepare ethene and/or propene, however, the olefinic co-feed preferably contains only olefins having 4 or more carbon atoms (i.e. $C_4+$ olefins), such as butenes, pentenes, hexenes and heptenes.

The olefinic co-feed is at least partly obtained form an olefinic refinery stream.

By an olefinic refinery stream is understood a stream containing one or more olefins derived from the product stream of a refinery unit. Examples of refinery units include thermal cracking units, catalytic cracking units, stream cracking units, butadiene extraction unit, C-5 olefinic extraction unit, semi-hydrogenation units for $C_4$ and/or $C_5$ diolefins units.

That is, the olefinic co-feed contains at least a fraction of olefins obtained or derived from a refinery unit.

Such a olefinic refinery stream may for example be derived from the product stream of a catalytic cracking unit or thermal cracking unit. Such cracking units in turn, can obtain their feed from the product streams of an atmospheric and/or vacuum distillation of a crude oil. Often the product stream of such an atmospheric and/or vacuum distillation is first treated, for example by hydrogenation, hydroisomerization or hydrocracking, before it is fed into the thermal-, catalytic- or stream cracking unit. A preferred catalytic cracking unit is a fluidized catalytic cracking unit.

In a preferred embodiment the olefinic refinery stream is derived from a fluidized catalytic cracking unit or stream cracking unit.

The product stream from a refinery unit is preferably separated into several fractions by distillation, whereafter an olefinic refinery stream is obtained that can be fed into the process according to the invention. Examples of suitable olefinic refinery streams include a $C_5$-olefinic stream obtained from cracking and (partial) hydrogenation of a dicyclopentadiene stream.

a $C_4$ and/or $C_5$-olefinic stream obtained after distillation from pyrolysis gasoline. Such a $C_4$ and/or $C_5$-olefinic stream (i.e. a stream containing olefins having 4 and/or 5 carbon atoms) can be partly hydrogenated before use in the process of the invention;

a $C_4$ and/or $C_5$ olefinic stream obtained after distillation of the product of a catalytic (e.g. fluidized) cracking unit.

In a stream cracker feeds such as for example naphtha (boiling e.g. between about 25° C. and about 180° C., preferably boiling between about 30° C. and about 160° C., more preferably boiling between about 35° C. and about 150° C.), gasoil (boiling e.g. between about 120° C. and about 370° C., preferably boiling between about 150° C. and about 300° C., more preferably boiling between about 180° C. and about 250° C.) and hydrowax or vacuum gasoil (boiling e.g. between about 200° C. and about 700° C., more preferably between about 250° C. and about 600° C.) are converted into lighter products.

The product stream of such a stream cracker can be distilled into several fractions. By a pyrolysis gasoline is understood a distillation fraction, boiling between $C_5$-205° C., preferably between 25° C. and 180° C., obtained after distillation of the product stream of such a stream cracker, such as for example illustrated in the Petroleum Handbook, 6th edition, compiled by the staff of the Royal Dutch/shell Group of Companies, published by Elsevier (1983), page 309.

The pyrolysis gasoline can be split into several product streams by for example distillation, extraction or other separation methods. One of these cuts may be a so-called "$C_5$-cut" (boiling between about 25° C. and 55° C.). Such a "$C_5$-cut" may be partially hydrogenated.

A partially hydrogenated "$C_5$-cut" can contain for example in the range from 0 to 1% w/w di-olefins; in the range from 10 to 95% w/w mono-olefins. The olefinic co-feed is at least partly obtained from an olefinic recycle stream.

By an olefinic recycle stream is understood a stream containing one or more olefins derived from the olefinic reaction mixture.

By an olefinic reaction mixture is understood a reaction mixture containing one or more olefins, i.e. including olefins prepared in the reaction.

Hence, the olefinic co-feed contains at least a fraction of recycled olefins separated from the olefinic reaction mixture.

In a preferred embodiment the process comprises the steps of
a) reacting an oxygenate feed and an olefinic co-feed in a reactor in the presence of zeolite catalyst
b) separating the olefinic reaction mixture into at least a first olefinic product fraction and a second olefinic fraction;
c) recycling at least part of the second olefinic fraction as an olefinic recycle stream;

wherein the olefinic co-feed is partially obtained from an olefinic refinery stream and partially obtained from the olefinic recycle stream.

The olefins in the olefinic co-feed preferably consist of in the range from 5 to 95 wt %, more preferably in the range from 10 to 90 wt %, based on the total weight olefins in the olefinic co-feed, olefins from an olefinic recycle stream and preferably in the range from 5 to 95 wt %, more preferably in the range from 10 to 90 wt % olefins, based on the total weight of olefins in the olefinic co-feed, olefins from an olefinic refinery stream.

By an oxygenate feed is understood a feed comprising one or more oxygenates. By an oxygenate is understood a compound comprising at least one oxygen-bonded alkyl group. The oxygen-bonded alkyl group preferably comprises 1 to 4 carbon atoms, more preferably 1 or 2 carbon atoms and most preferably 1 carbon atom. The oxygenate can comprise one or more of such oxygen-bonded $C_1$-$C_4$ alkyl groups. Preferably, however, the oxygenate comprises one or two oxygen-bonded $C_1$-$C_4$ alkyl groups. Examples of preferred oxygenates include alcohols, such as methanol, ethanol, isopropanol, ethylene glycol, propylene glycol; and ethers, such as dimethylether, diethylether, methylethylether, tetrahydrofuran and dioxane.

Preferably the oxygenate is chosen from the group of dimethylether, diethylether, methylethylether, methanol, ethanol and isopropanol.

More preferably an oxygenate is used having at least one oxygen-bonded $C_1$ or $C_2$ alkyl group, still more preferably at least one oxygen-bonded $C_1$ group. Most preferably the oxygenate is methanol or dimethylether.

In a preferred embodiment, where the oxygenate is methanol, such methanol is obtained from natural gas. For example by a process as described in Industrial Organic Chemistry 3rd edition page 28.

In another preferred embodiment the oxygenate is obtained through fermentation of biomaterials. For example by a process as described DE-A-10043644.

The preferred molar ratio of oxygenate in the oxygenate feed to olefin in the olefinic co-feed depends on the specific oxygenate used and the number of reactive oxygen-bonded alkyl groups therein. An alcohol compound comprises one such oxygen-bonded alkyl group, whereas an ether comprises two such oxygen-bonded alkyl groups.

Preferably the ratio of mol oxygen-bonded alkyl groups to mol lower olefin lies in the range of 10:1 to 1:1, more preferably in the range of 5:1 to 1:1 and still more preferably in the range of 3:1 to 1:1. In a preferred further embodiment a molar ratio is used of more than 1:1, more preferably a ratio of 1.5:1.

In a preferred embodiment wherein the oxygenate comprises only one oxygen-bonded alkyl group, such as for example methanol or ethanol, the molar ratio preferably lies in the range from 5:1 to 1:5 and more preferably in the range of 2:1 to 1:2. Most preferably the molar ratio in such a case is about 1:1.

In another preferred embodiment wherein the oxygenate comprises two oxygen-bonded alkyl group, such as for example dimethylether, the molar ratio preferably lies in the range from 5:2 to 1:10 and more preferably in the range of 1:1 to 1:4. Most preferably the molar ratio in such a case is about 1:2.

The process is carried out in presence of zeolite catalyst. By a zeolite catalyst is understood a catalyst comprising a zeolite, optionally in combination with a binder.

Preferably, the zeolite is a zeolite comprising a 10-membered ring channel. More preferably this zeolite is a one-dimensional zeolite having 10-membered ring channels.

These are understood to be zeolites having only 10-membered ring channels in one direction which are not intersected by other 8, 10 or 12-membered ring channels from another direction.

One suitable zeolite is a zeolite of the MFI-type (for example ZSM-5). Preferably, however, the zeolite is selected from the group of TON-type (for example ZSM-22), MTT-type (for example ZSM-23), STF-type (for example SSZ-35), SFF-type (for example SSZ-44) and EU-2-type/ZSM-48 zeolites.

MTT-type catalysts are more particularly described in e.g. U.S. Pat. No. 4,076,842. For purposes of the present invention, MTT is considered to include its isotypes, e.g., ZSM-23, EU-13, ISI-4 and KZ-1.

TON-type zeolites are more particularly described in e.g. U.S. Pat. No. 4,556,477. For purposes of the present invention, TON is considered to include its isotypes, e.g., ZSM-22, Theta-1, ISI-1, KZ-2 and NU-10.

EU-2-type zeolites are more particularly described in e.g. U.S. Pat. No. 4,397,827. For purposes of the present invention, EU-2 is considered to include its isotypes, e.g., ZSM-48.

In a further preferred embodiment a zeolite of the MTT-type, such as ZSM-23, or a TON-type, such as ZSM-22 is used.

Preferably a zeolite in the hydrogen form is used, e.g., HZSM-22, HZSM-23, H-ZSM-35 and HZSM-48. Preferably at least 50% w/w, more preferably at least 90% w/w, still more preferably at least 95% w/w and most preferably 100% of the total amount of zeolite used is zeolite in the hydrogen form. When the zeolites are prepared in the presence of organic cations the zeolite may be activated by heating in an inert or oxidative atmosphere to remove the organic cations, for example, by heating at a temperature over 500° C. for 1 hour or more. The hydrogen form can then be obtained by an ion exchange procedure with ammonium salts followed by another heat treatment, for example in an inert or oxidative atmosphere at a temperature over 500° C. for 1 hour or more. The latter zeolites are also referred to as being in the ammonium form.

Preferably the zeolite has a silica to alumina ratio (SAR) in the range from 1 to 500. Preferably the zeolite has a SAR in the range from 10 to 200.

The zeolite can be used as such or in combination with a so-called binder material. When used in the reaction, the zeolite as such or the zeolite in combination with a binder material, are hereafter also referred to as zeolite catalyst.

It is desirable to provide a catalyst having good crush strength, because in an industrial environment the catalyst is often subjected to rough handling, which tends to break down the catalyst into powder-like material. The later causes problems in the processing. Preferably the zeolite is therefore incorporated in a binder material. Examples of suitable binder materials include active and inactive materials and synthetic or naturally occurring zeolites as well as inorganic materials such as clays, silica, alumina, aluminosilicate. For present purposes, inactive materials of a low acidity, such as silica, are preferred because they may prevent unwanted side reactions which may take place in case a more acidic material, such as alumina is used. Preferably the catalyst used in the process of the present invention comprises, in addition to the zeolite, 2 to 90 wt %, preferably 10 to 85 wt % of a binder material.

The process of the present invention can be carried out in a batch, continuous, semi-batch or semi-continuous manner. Preferably the process of the present invention is carried out in a continuous manner.

If the process is carried out in a continuous manner, the process may be started up by using olefins obtained from an external source for the olefinic co-feed in step a). Such olefins may for example be obtained from a stream cracker, a catalytic cracker, alkane dehydrogenation (e.g. propane or butane dehydrogenation). Further, such olefins can be bought from the market.

In a special embodiment the olefins for such start-up are obtained from a previous process that converted oxygenates, with or without olefinic co-feed, to olefins. Such a previous process may have been located at a different location or it may have been carried out at an earlier point in time.

In another embodiment an additional catalyst may be used as initiator. After the start-up phase such an initiating catalyst can be removed. Suitable catalysts for this initiating purpose include for example MFI-type catalysts and SAPO-type catalysts.

The reactor used in step a) may be any reactor known to the skilled person and may for example contain a fixed bed, moving bed, fluidized bed and the like.

Conventional catalyst regeneration techniques can be employed. The one-dimensional zeolite having 10 membered ring channels used in the process of the present invention can have any shape known to the skilled person to be suitable for this purpose, for it can be present in the form of tablets, rings, extrudates, etc. extruded catalysts can be applied in various shapes, such as, cylinders and trilobes. If desired, spent zeolite can be regenerated and recycled to the process of the invention.

The process can be carried out over a wide range of temperatures and pressures. Preferably, however, the oxygenate feed and the olefinic co-feed are contacted with the zeolite at a temperature in the range from 200° C. to 550° C., more preferably in the range from 225° C. to 525° C., still more preferably in the range from 250° C. to 450° C. and at an absolute pressure in the range from 1 to 5 bar, more preferably in the range from 1 to 3 bar.

Preferably the oxygenate feed and olefinic co-feed are fed to the process according to the invention as a vapour, preferably diluted with a diluent gas. Preferably such a diluent gas is an inert gas, such as for example nitrogen or argon. For example, the oxygenate feed and/or olefinic co-feed can be diluted with stream, for example in the range from 0.01 to 10 kg stream per kg feed.

In a further preferred embodiment small amounts of water are added in order to improve the stability of the catalyst by reducing coke formation.

As described above the process according to the invention may comprise a separation step. Preferably the olefinic reaction mixture (e.g. step a) is separated into at least a first olefinic product fraction and a second olefinic fraction ((e.g. step b). In a further step (e.g. step c) at least part of the second olefinic fraction obtained (e.g. in step b) is recycled (e.g. to step a) as an olefinic co-feed.

The separations can be carried out by any method known to the skilled person in the art to be suitable for this purpose, for example by vapour-liquid separation (e.g. flashing), distillation, extraction, membrane separation or a combination of such methods. Preferably the separations are carried out by means of distillation.

The process has been illustrated in FIG. 1. Herein a crude oil (1) is distilled in an atmospheric distillation unit (crude distiller), the long residue fraction (2) obtained from this distillation unit is fed into a high vacuum unit (HVU), in order to obtain a flashed distillate (3). This flashed distillate (3) is fed into a catalytic cracking unit (CCU). The product of this catalytic cracking unit is separated into several fractions, one of the fraction containing $C_4$ olefins (4). The $C_4$ olefins (4) are fed together with an oxygenate feed (5) into an olefins conversion process (i.e. an example of the process according to the invention). The product of this olefins conversion process is separated into a $C_4+$ fraction, containing for example butenes, a $C_2/C_3$ fraction containing ethylene and/or propylene, and a water fraction. The $C_4+$ fraction is recycled.

What is claimed is:

1. A process for the preparation of ethylene and/or propylene comprising reacting an oxygenate feed, wherein the oxygenate comprises at least one oxygen-bonded alkyl group, and an olefinic co-feed in a reactor in the presence of an MTT zeolite catalyst, wherein the zeolite is in the hydrogen form and has a SAR in the range from 10 to 200, to prepare an olefinic reaction mixture;
   a) separating the olefinic reaction mixture into at least a first olefinic product fraction comprising a $C_2/C_3$ fraction containing ethylene and/or propylene and a second olefinic fraction comprising $C_{4+}$ olefins; and
   b) recycling at least part of the second olefinic fraction as an olefinic recycle stream;
   wherein the olefinic co-feed is partially obtained from an olefinic refinery stream and partially obtained from a olefinic recycle stream.

2. The process according to claim 1, wherein the oxygenate is methanol or dimethylether.

3. The process according to claim 1, wherein ethene and/or propene are prepared, and wherein the olefinic co-feed comprises only olefins having 4 or more carbon atoms.

4. The process according to claim 1, wherein the ratio of mol oxygen-bonded alkyl groups in the oxygenate feed to mol olefin in the olefinic co-feed is more than 1:1.

5. The process according to claim 1, wherein the olefinic co-feed comprises more than 50 wt % of olefin(s).

6. The process according to claim 1, wherein the olefinic co-feed consists essentially of olefin(s).

7. The process according to claim 1, wherein the olefinic refinery stream is derived from a fluidized catalytic cracking unit.

8. The process according to claim 1, wherein the olefins have in the range from 4 to 12 carbon atoms.

9. The process according to claim 1, wherein the olefinic co-feed comprises from 5 to 95 wt %, based on the total weight olefins in the olefinic co-feed, olefins from the olefinic recycle stream, and in the range from 5 to 95 wt %, based on the total weight of olefins in the olefinic co-feed, olefins from the olefinic refinery stream.

10. The process according to claim 1, wherein waste olefins are provided to the process as a non-continuous stream.

* * * * *